United States Patent [19]

Boesig et al.

[11] Patent Number: 4,511,553

[45] Date of Patent: Apr. 16, 1985

[54] COATING PROCESS AND AGENT FOR CARRYING OUT THE PROCESS

[75] Inventors: Werner Boesig, Garmisch-Partenkirchen; Bernd Pritzwald-Stegmann, Edling, both of Fed. Rep. of Germany

[73] Assignee: Meggle Milchindustrie GmbH & Co. KG, Reitmehring, Fed. Rep. of Germany

[21] Appl. No.: 604,406

[22] Filed: Apr. 27, 1984

Related U.S. Application Data

[63] Continuation of Ser. No. 181,570, Aug. 27, 1980, abandoned.

[30] Foreign Application Priority Data

Sep. 6, 1979 [DE] Fed. Rep. of Germany ....... 2936040

[51] Int. Cl.$^3$ ................................................ A61K 9/36
[52] U.S. Cl. ..................................... 424/35; 426/302; 426/309; 427/3
[58] Field of Search .............. 424/35; 427/3; 426/302, 426/309

[56] References Cited

U.S. PATENT DOCUMENTS 3,406,031 10/1968 Lee .................................... 424/35 X
3,798,054 3/1974 Kawata et al. ......................... 424/35

Primary Examiner—Richard A. Schwartz
Attorney, Agent, or Firm—Felfe & Lynch

[57] ABSTRACT

A coating process and agent for carrying out the process, consisting essentially of saccharose, at least one additional sugar and water.

5 Claims, No Drawings

COATING PROCESS AND AGENT FOR CARRYING OUT THE PROCESS

This is a continuation application of U.S. Ser. No. 181,570, filed Aug. 27, 1980 now abandoned.

The present invention relates to a process for coating cores, such as the cores of pharmaceutical dragées, chocolate centers, hazelnuts, and the like, with a coating agent consisting essentially of saccharose, at least one additional sugar, and water. Coating processes for covering the cores of tablets or pills with a hard layer of sugar are in themselves familiar; cf. Ullmann's *Enzyklopadie der technischen Chemie*, third edition. Volume 4, page 10, and Volume 19, page 260. In the process, the layer of sugar is put into the coating kettle, which has been filled with the cores of dragées, in the form of a liquid syrup. As a result of turning the coating kettle, all the cores of the dragées are covered with a liquid film of sugar. As soon as this has taken place (after about 1 minute), warm or cold air is blown into the kettle, and the thin film turns solid. This operation is repeated 20 to 50 or even 80 times, as desired.

In the familiar processes for coating cores or pills with layers of sugar, aqueous solutions of saccharose are used as coating agents, to which flavors, fragrances, coloring matter and/or adjuvants are added, according to the intended use. Such saccharose solutions tend to premature crystallization in the course of the coating process. In the commercial process, this difficulty is avoided either by reheating the solution, or by simply skimming the clear solution from the crystals in the supply tank and putting it into the coating kettle. In the process, however, the coating solution is reduced in strength by the fraction of crystallized sugar.

In modern industrial processes, the coating process is more or less automated. If a continuous process is used, the solution must be pumped from the supply tank into the coating kettle. On the way from the supply tank to the coating kettle, the solution can cool off, under certain circumstances, and the danger then exists that the saccharose will crystallize in the piping system. Cleaning up such a breakdown is only possible by dismantling the piping system and rinsing. Crystallization must, therefore, be avoided under any circumstances.

It is just in continuous, industrial coating processes, therefore, that it is important to use those coating agents containing saccharose from which no saccharose will crystallize out, even if there is a certain amount of cooling. In the known coating processes with coating agents consisting essentially of saccharose, however, the undesirable occurrence of the crystallization of saccharose occasionally took place.

According to the present invention, a coating process and a coating agent for carrying it out have now been produced, in which the tendency of saccharose to crystallize has been very considerably reduced.

The subject of the present invention is, thus, a process for coating cores, such as the cores of pharmaceutical dragées, chocolate centers, hazelnuts, and the like, with a coating agent consisting essentially of saccharose, at least one additional sugar, and water, characterized in that the centers are coated with a coating agent, in which the additional sugar constituent is lactose, in a manner that is in itself familiar.

In a preferred form of carrying out the process according to the present invention, a coating agent is used, in which the proportion by weight of saccharose to lactose is between 90:10 and 50:50; in a particularly preferred form of carrying it out, the proportion by weight of saccharose to lactose is between 80:20 and 70:30.

An additional subject of the present invention is a coating agent for carrying out the process, characterized in that the proportion by weight of saccharose to lactose is between 90:10 and 50:50; combinations within this range are preferred. Especially preferred is a composition of the agent that is essentially characterized in that the proportion by weight of saccharose to lactose is beween 80:20 and 70:30.

The coating processes that can be carried out with the coating agent according to the present invention are in themselves familiar; cf., for example, Ullman, *Enzyklopadie der technischen Chemia*, third edition, Volume 4, page 10 and Volume 19, page 260. The process according to the present invention is carried out in a manner that is itself familiar, with a coating agent that, in addition to saccharose, also contains lactose as a further sugar constituent. The term essentially here means that "the coating agent according to the present invention may contain, in addition to the principal constitutents indicated, saccharose, lactose, and water, relatively small amounts, too, of the usual admixed materials and adjuvants." Thus, the coating agent according to the present invention, which consists essentially of saccharose, lactose, and water, also contains, as a rule, the usual flavors, fragrances, and coloring matter as additional constituents, in adaptation to the intended use in each case.

Peppermint oil and, especially, vanillin, for example, are considered here as flavors and fragrances.

Suitable coloring substances are food colors, such as, woodruff green, raspberry red, lemon yellow, pistachio green, cherry red, and others, These coloring substances are usually added to the coating agent in the form of a dilute aqueous solution.

An important advantage that is offered by the process of the present invention and the coating agent for carrying it out is the considerably reduced tendency of a sugar—no matter whether saccharose and/or lactose—to crystallize out under ordinary coating conditions. The considerably lower tendency to crystallize out in the practical carrying out of the crystallization process according to the present invention is demonstrated by comparison tests according to Examples 1 to 3. In Example 4, saccharose/water and saccharose/lactose/water solutions of graduated combinations were cooled from 108° C. to room temperature, and the length of time up to the beginning of crystallization was measured. The tests showed that the combinations corresponding to claims 4 and 5 (namely, the tests according to Table 1, with 900 g of saccharose/100 g of lactose/350 ml of H$_2$O and 700 g of saccharose/300 g of lactose/350 ml of H$_2$O) demonstrated a longer period up to the beginning of crystallization, or no crystallization appeared at all. It is surprising that the effect of delaying the beginning of crystallization of such highly concentrated saccharose solutions is possible at all, and that this effect is produced by the very addition of the sugar lactose, which is little soluble in water. For this effect appears even though lactose, in comparison with saccharose, is much less soluble in water.

A further advantage that can be achieved through the present invention is to be seen in the fact that the taste of the covering of the dragée is changed by the lactose fraction, and consequently can be changed. The sweetness is, namely, reduced by replacing a part of the saccharose with lactose, although in so doing, the amount of sugar itself remains the same. In some cases, however, reduced sweetness in dragées is desirable.

An additional advantage can be achieved by means of the present invention: in contrast to the usual process, it is now possible to carry out the actual coating process, that is, the covering of the core with the sugar mass, at significantly lower temperatures than usual, which is made possible by the reduced tendency to crystallization of the coating agent according to the present invention.

The following examples illustrate the invention:

EXAMPLE 1

5 kg of cores for pharmaceutical dragées (lactose placebos of 98.5% lactose, 0.5% magnesium stearate, and 1.0% microcellulose) were coated in a coating kettle with a maximal filling quantity of 10 kg with a 50% actual filling quantity.

The coating agent of 900 mg of saccharose, 100 g of lactose, 350 ml of water, and 10 ml of aqueous raspberry red solution was prepared by first dissolving 100 g of lactose in 350 ml of water and heating to a clear solution, and then 900 g saccharose, in medium-fine granules, was added. After boiling briefly at 108° C. in an open copper kettle, everything was dissolved, and after cooling the solution down to 90° C., coating was begun.

100 ml of the coating agent solution was applied to 5 kg of pharmaceutical dragée cores. Drying of the film of sugar solution (the covering) on the dragée core was carried out with hot air having a temperature of 40° C. After about 5 minutes, the coat was dry, and the second coat was applied in the form of an additional 100 ml charge of the coating agent solution. Then drying was carried out again for about 5 minutes. From the third coat on, the work was carried out with a reduced quantity of the liquid, namely, 40 ml of coating agent solution for the second to sixth layers, 45 ml for the seventh to eighth layers, 50 ml for the ninth to eleventh layers, 55 ml for the twelfth to fourteenth layers, and 45 ml, with the addition of 10 ml of hot water, for the fifteenth layer. Care had to be taken that no hot air was applied while the liquid was being received, so that it spread over the surface better. The coating procedure was carried out in this form, as described, up to coat number 15. With the last coat, the charge of solution was diluted somewhat, and in this way, a somewhat smoother dragée coating was achieved. After coating, the finished dragées were laid out on wickerwork carts for further drying.

No crystallization from the coating agent solution, which was at a temperature of 90° C., could be observed in the supply tank. The test was repeated with a changed proportion by weight of saccharose to lactose, namely, 800 g of saccharose/200 g of lactose (1b), 700 g of saccharose/300 g of lactose (1c), and 500 g of saccharose/500 g of lactose (1d). In tests 1b and 1c, no crystallization appeared either; in test 1d, it did not appear until after one hour.

A comparison test with a coating agent solution of 1,000 g of saccharose alone, carried out in the same manner, showed that crystallization from the coating agent solution, which was at a temperature of 90° C., was already beginning in the supply tank after 10 minutes.

EXAMPLE 2

15 kg of chocolate centers was hard coated, in a manner analogous to that in Example 1. In a deviation from this, however, drying was carried out with air that was at room temperature, in order not to cause melting of the chocolate, and with the use of a coating kettle with a 30 kg maximal filling quantity. Two charges (Examples 2a and 2b) were run with two different coating agent solutions. The two coating agent solutions used consisted of (2a)

3.5 kg of saccharose,
1.5 kg of lactose,
1.7 l of water, and
10 ml of peppermint oil or (2b)

2.5 kg of saccharose,
2.5 kg of lactose,
1.7 l of $H_2O$,
30 ml of aqueous raspberry red solution
10 ml of peppermint oil
and were prepared as in Example 1.

80 dragée coats were provided in each case. At the end, three covering layers were applied in a familiar manner, with a solution of soaked gelatine, saccharose, and water, as well as a last layer of syrup and water.

By so doing, chocolate centers with a relatively hard outer layer of sugar are obtained.

In Example 2b, no crystallization took place in the supply tank from the hot coating agent solution; in Example 2b, a slight crystallization began after 2.5 hours.

EXAMPLE 3

13 kg of hazelnuts that had already been covered (roasted, sweetened, thickened) were soft-coated. Soft-coating means that, in a manner analogous to hard-coating, a sugar solution (coating agent solution) is boiled; however, after adding a specific solution to the product in the dragée kettle, the coating is not dried with hot air, but with sugar, for example, saccharose or also lactose. It is dusted, and the excess moisture is partly evaporated, and partly allowed to go into the sugar that has been used for dusting. Two charges (Examples 3a and 3b) were run, with two different coating agent solutions. The two coating agent solutions, consisiting of (3a)

3.5 kg of saccharose,
1.5 kg of lactose,
1.7 l of water,
50 ml of aqueous cola brown solution, and
5 g of vanillin, or (3b)

2.5 kg of saccharose,
2.5 kg of lactose,
1.7 l water,
50 ml of aqueous yellowish solution, and
5 g of vanillin
were prepared as in Example 1.

10 coats were provided in each case, and each coat was dusted with saccharose immediately after coating.

In Example 3a, no crystallization took place from the hot coating agent solution in the supply tank; in Example 3b, there was delayed crystallization in comparison with conventional processes.

EXAMPLE 4

The constituents saccharose/water or saccharose/lactose/water in various quantitative proportions (cf. Table 1, Column 1) were boiled at 108° C. until everything had dissolved, and the crystallization properties were investigated upon cooling or at constant temperature.

The hot solutions were allowed to cool in a beaker to room temperature, here 26° C., with stirring (45 rpm) or without. At the same time, it was observed whether or when there was crystallization. The tests were stopped after a maximum of twenty hours. Table 1, Column 2 shows how long before crystallization took place, if at all, and at what temperature.

1,350 kg of each solution, according to Column 1 of Table 1 was placed, after preparation by boiling at 108° C., in a supply tank for coating agent solutions in a semicommercial coating plant (V=15 liters), and the solution was allowed to cool off there. Here, too, observations were made within a period of 3 hours of whether and, if so, after how many minutes, the first crystallization appeared. The results are entered in Table 1, Column 3.

Even with cooling to 20° C., the solution did not crystallize out after 5 hours. The coating proceeded without problems.

(b) A test with a sugar solution of 70% saccharose and 30% lactose 700 g of saccharose/200 g of lactose/350 ml of H$_2$O), with a boiling temperature of 106° C.

This solution worked very well in the processing. After a 2-hour coating process, there was still no evidence of crystallization of the syrup in the supply tank.

(c) A comparison test with a pure saccharose solution (1,000 g of saccharose/350 ml of H$_2$O), with a boiling temperature of 108° C.

Upon cooling to about 70° C., the solution began to crystallize out after 10 minutes. Coating with this solution was possible only within limits.

We claim:

1. In a process for coating cores of pharmaceutical dragées, chocolate centers, and hazelnuts, with a saccharose coating agent; the improvement comprising mixing the saccharose with lactose in a proportion by weight of 90:10 to 50:50, and with water to form the coating agent, and thereafter coating the centers with the coating agent.

2. A process according to claim 1, characterized in that the coating is done with a coating agent in which the proportion by weight of saccharose to lactose is

TABLE 1

Crystallization Properties upon Cooling from the Boiling Temperature (108° C.) to Room Temperature

| Constituents of the Solution | | | Laboratory Test Beginning of Crystallization | | Operational Test |
|---|---|---|---|---|---|
| Saccharose (g) | Lactose (g) | Water (ml) | with stirring (Time, Temp) | without stirring (Time, Temp) | Beginning of Crystallization (after minutes) |
| 1000 (= comparison) | — | 350 | 20′, 67° | 35′, 55° | 10′, strong |
| 900 | 100 | 350 | 65′, 47° | 90′, 40° | — |
| 800 | 200 | 350 | 300′, 29° | 960′, 27° | — |
| 700 | 300 | 350 | — 26° | — 26° | — |
| 600 | 400 | 350 | 30′, 58° | 30′, 58° | — |
| 500 | 500 | 350 | 30′, 58° | 30′, 58° | 60′ |

EXAMPLE 5

Coating Tests with Variation of the Saccharose/Lactose Proportion

Pharmaceutical dragée cores (placebos of 98.5% lactose, 0.5% magnesium stearate, and 1% microcellulose) were coated in a unit as described in Example 1. The kettle gradient was 37°; the rate of the kettle's revolution was 30 rpm. The temperature of the hot air that was blown into it was 40° C. The moist running time was one minute; the drying period about 2.5 minutes.

(a) A test with a sugar solution of 80% saccharose and 20% lactose (800 g of saccharose/200 g of lactose/350 ml of H$_2$O), with a boiling temperature of 108° C.

between 80:20 and 70:30.

3. In a sugar coating agent for coating cores of pharmaceutical dragées, chocolate centers, and hazelnuts, the improvement comprising using a mixture consisting essentially of saccharose and lactose in a proportion by weight of saccharose to lactose of between 90:10 and 50:50 as the sugar component.

4. A coating agent according to claim 3, characterized in that the proportion by weight of saccharose to lactose is between 80:20 and 70:30.

5. In a process for coating cores of pharmaceutical dragées, chocolate centers, and hazelnuts with a saccharose coating agent, the improvement comprising using a core coating agent consisting essentially of saccharose and lactose in a proportion by weight of 90:10 to 50:50, to coat the cores.

* * * * *